United States Patent [19]
Pagé et al.

[11] Patent Number: 5,981,564
[45] Date of Patent: Nov. 9, 1999

[54] WATER-SOLUBLE DERIVATIVES OF PACLITAXEL, METHOD FOR PRODUCING SAME AND USES THEREOF

[75] Inventors: Michel Pagé; Renée Paradis; Cyrille Bicamumpaka, all of Québec, Canada

[73] Assignee: Universite Laval, Quebec, Canada

[21] Appl. No.: 09/108,585

[22] Filed: Jul. 1, 1998

[51] Int. Cl.$^6$ .............. A61K 31/27; A61K 34/415; C07D 233/64; C07D 305/14
[52] U.S. Cl. .............. 514/400; 514/480; 548/339.1; 549/510; 562/562; 562/563; 562/570; 562/573
[58] Field of Search ............ 514/400, 480; 549/510; 548/339.1; 562/562, 563, 570, 573

[56] References Cited

U.S. PATENT DOCUMENTS 4,960,790 10/1990 Stella et al. .

OTHER PUBLICATIONS

Borman et al.. 1994, C & EN, 21:32–4.
Cardellina II, 1991, J Liq Chromatogr 14:659–65.
Deutsch et al., 1989, J Med Chem, 32:788–92.
Haldar et al., 1997, Cancer Res, 57:229–33.
Kingston, 1991, Pharmac Ther, 52:1–34.
Kingston et al., 1990, J Nat Prod, 53:1–12.
Martin et al., 1990, Cell Tissue Kinet, 23:545–59.
Mathew et al., 1992, J Med Chem, 35:145–51.
Page et al., 1993, Intl J Oncol, 3:473–6.
Rowindky et al., 1990, J Nat Can Inst, 82:1247–58.
Swindell et al., 1991, J Med Chem, 34:1176–84.
Turgeon et al., 1992, Drug Metabolism and Disposition, 20:762–9.

*Primary Examiner*—Johann Richter
*Assistant Examiner*—Taofiq A. Solola
*Attorney, Agent, or Firm*—Klauber & Jackson

[57] ABSTRACT

The invention relates to new paclitaxel derivatives showing an increased solubility in water. More particularly, the invention relates to glutarylpaclitaxel, glutarylpaclitaxel 6-aminohexanol glucuronide and to different amino acid derivatives of the glutarylpaclitaxel, all of which possess the cytotoxicity activity of the parent compound, paclitaxel. Also disclosed are fluorescent derivatives of paclitaxel for determining a concentration of paclitaxel in a medium or for detecting apoptotic cancer cells.

19 Claims, 12 Drawing Sheets

WATER-SOLUBLE DERIVATIVES OF PACLITAXEL, METHOD FOR PRODUCING SAME AND USES THEREOF

BACKGROUND OF THE INVENTION (a) Field of the Invention

The invention relates to new paclitaxel derivatives showing an increased solubility in water.

(b) Description of Prior Art

Paclitaxel is a natural product extracted from the bark of the Pacific yew (*Taxus brevifolia*). It was thereafter found in other members of the Taxacae family including the yew of Canada (*Taxus canadensis*) found in Gaspesia, eastern Canada and *Taxus baccata* found in Europe whose needles contain paclitaxel and analogs and hence provide a renewable source of paclitaxel and derivatives. The crude extract was tested for the first time during the 60s and its active principle was isolated in 1971 by Wani et al. who at the same time identified its chemical structure. It showed a wide range of activity over melanoma cells, leukemia, various carcinomas, sarcomas and non-Hodgkin lymphomas as well as a number of solid tumors in animals. Clinical studies show that paclitaxel is a promising anti cancer agent. Paclitaxel is a microtubule blocker, but unlike other drugs inhibiting the mitosis by interaction with microtubules such as colchicin, vincristin and podophyllotoxin, paclitaxel does not prevent tubulin assembly. It rather accelerates the tubulin polymerization and stabilizes the assembled microtubules. The drug acts in a unique way which consists in binding to microtubules, preventing their depolymerization under conditions where usually depolymerization occurred (dilution, calcium, cold and microtubules disrupting drugs). Paclitaxel blocks the cell cycle at prophase which results in an accumulation of cells in G2+M. Because of its unique structure and mechanism of action, paclitaxel was submitted to clinical trials. Interesting activity against many tumors, especially breast cancer and ovarian cancer refractory to chemotherapy, has been observed. However, because of its poor solubility in water, the product had to be administered in ethanol, Cremophor-EL and 5% sucrose diluted in saline or water. Cremophor-EL was responsible for hypersensitivity reactions observed in several patients (Rowinsky, E. K., et al., *J. Nat. Can. Inst.*, 82 (15), 1247–1259). Premedication with anti-histamines had to be administered in order to reduce the toxicity.

Poor solubility of paclitaxel constitutes an important limitation to its administration to cancer patients. To increase paclitaxel availability, total and partial synthesis have been reported. The improvement of paclitaxel solubility was obtained by adjunction of solubilizing functions such as carbonyl or sulfonyl groups with good results. Some of the synthesized products were more active than paclitaxel, many others had a biological activity equivalent or slightly inferior to that of paclitaxel while being far more soluble in water (KINGSTON, D. G., *Pharmacol. Ther.* (England), 52(1) p1–34, 1991). The complexity of the paclitaxel chemical structure rendered its total synthesis very difficult until recently when it was achieved simultaneously by two different groups. However the yield of this synthesis of the order of 2–4% will have little impact on the paclitaxel availability (BORMAN, S., Total synthesis of anticancer agent paclitaxel was achieved by two different routes (C@EN. February, 32–34, 1994)).

Many attempts have been made to improve paclitaxel aqueous solubility with various components resulting in poorly stable products or inactive ones. Moreover, sometimes the synthesis of these compounds required many chemical steps.

Paclitaxel has three hydroxyl groups at carbon 1, 7 and 2' susceptible of undergoing an acylation. Their reactivity varies according to the following order: 2'>7>>>1 (MATHEW, A. E., et al., *J. Med. Chem.*, 35, 145–151, 1992). Acylation on 2'C is the best way of paclitaxel modification because of its great reactivity, and because even if 2' acylpaclitaxels loose their property of promoting the microtubules polymerization in vitro, they are hydrolyzed in the cell and revert to paclitaxel and keep their cytotoxic activity (KINGSTON, D. G., et al., *J. Nat. Prod.*, 1–13, 1990; and MELLADO, W., et al., *Biochem. Biophys. Res. Commun.*, 105, 1082–1089, 1984).

Accordingly, to increase solubility, several derivatives have been synthesized by modification of the 2' or/and 7 hydroxyls. The 2' hydroxyl appears as a good candidate for chemical modification. The 7 hydroxyl requires more drastic conditions to react while the tertiary hydroxyl in position 1 is inert. The 2' and 7 hydroxyls have been modified with several groups (Deutsch, H. M., et al., *J. Med. Chem.*, 32, 788–792, 1989; Rose, W. C., et al., *Cancer Chemother. Pharmacol.*, 39, 486, 1997) but only a few derivatives were synthesized with a sugar moiety as reported by Kingston et al. (Kingston, D. G. I., *Pharmac. Ther.*, 52, 1–34, 1991). However, many derivatives were insufficiently soluble, inactive or too unstable to be applied in a clinical situation.

It would be highly desirable to be provided with new active paclitaxel derivatives having improved solubility with respect to paclitaxel.

It would be highly desirable to be provided with a simple, rapid and accurate immunological method for the measurement of paclitaxel in biological fluids and in Taxus crude extracts.

It would be highly desirable to be provided with a fluorescent derivative of paclitaxel, which binds to microtubules, to discriminate apoptotic cells.

SUMMARY OF THE INVENTION

One aim of the present invention is to provide a new active paclitaxel derivative modified at the 2'- or 7 position showing improved solubility.

Another aim of the present invention is to provide new paclitaxel derivatives made from glutarylpaclitaxel to which different amino acids or glucuronide were conjugated. These new compounds show cytotoxic activity similar to paclitaxel alone but with an improved aqueous solubility.

Another aim of the present invention is to provide a method for detecting apoptosis of cells.

Another aim of the present invention is to provide fluorescent derivatives of paclitaxel for the measurement of paclitaxel in biological specimens and in extracts of different Taxus species, with high sensitivity using a FPIA (Fluorescent Polarization ImmunoAssay).

Another aim of the present invention is to provide a method and a kit for the detection of paclitaxel in a medium.

Another aim of the present invention is to provide a method for the in vivo treatment or prophylaxis of cancer comprising the step of administering a therapeutically effective amount of a water-soluble paclitaxel derivative as defined above to a patient in need of such a treatment.

Another aim of the present invention is to provide a method for in vitro or in vivo labeling tubulin comprising the step of contacting patient's cells with a water-soluble derivative of paclitaxel as defined above.

Another aim of the present invention is to provide a in vitro method for determining apoptosis of cancer cells comprising the steps of:
a) incubating cells with a labeled paclitaxel derivative under suitable condition for the derivative to penetrate in the cells, whereby the labeled paclitaxel derivative binds to microtubules of cancer cells, thereby preventing cell division;
b) washing off the cells from unbound labeled paclitaxel derivative; and
c) detecting a label on the labeled paclitaxel derivative bound to cancer cell, whereby detection of the label is indicative of apoptotic cancer cells.

Another aim of the present invention is to provide a pharmaceutical composition comprising a derivative as defined above with a pharmaceutically acceptable carrier.

In accordance with the present invention there is provided a water-soluble paclitaxel derivative or a salt thereof having the following Formula I:

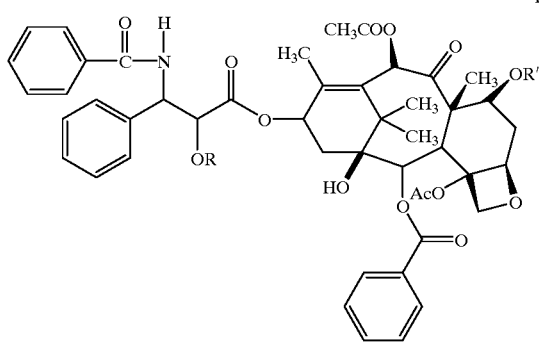

wherein R and R', identical or different, are a hydrogen or a —CO—(CH$_2$)$_3$—COX, in which X is selected from the group consisting of a hydroxyl, a 6-aminohexanol group, a 1,6-diaminohexyl, and a polar amino acid residue, and with the proviso that R and R' are not both hydrogen. Preferably, R or R' is a hydrogen.

Preferably, the polar amino acid residue is selected from the group of residues consisting of arginine, asparagine, aspartic acid, cystein, glutamic acid, glutamine, glycine, histidine, lysine, phenylalanine, serine, threonin and tyrosine. More preferably, the polar amino acid residue is asparagine or glutamine residue.

The paclitaxel derivative in accordance with one embodiment of the invention is labeled with a marker, such as without limitation, a fluorescent marker or a radioactive marker.

In accordance with the present invention, there is provided a derivative as described above, on which a glucuronide moiety is connected to the 6-aminohexanol group.

In accordance with the present invention, there is also provided a method for the in vivo treatment or prophylaxis of cancer comprising the step of administering a therapeutically effective amount of a water-soluble paclitaxel derivative as defined above to a patient in need of such a treatment.

In accordance with the present invention, there is also provided a method for in vitro or in vivo labeling of tubulin comprising the step of contacting patient's cells with a water-soluble derivative of paclitaxel as defined above.

In accordance with the present invention, there is further provided a method for in vitro determining the concentrations of paclitaxel or paclitaxel derivative comprising the steps of:

a) contacting a labeled paclitaxel derivative, preferably a fluorescent labeled derivative, with a biological fluid or a crude extract from a Taxus species, and an antibody raised against paclitaxel, whereby said labeled paclitaxel derivative competes for said antibody against paclitaxel in said biological fluid or said crude extract;
b) detecting a label on said labeled paclitaxel derivative; and
c) determining the quantity of paclitaxel from said biological fluid or said extract with respect to a standard competition curve.

In accordance with the present invention, there is further provided an in vitro method for determining apoptosis of cancer cells comprising the steps of:
a) incubating cells with a labeled paclitaxel derivative, preferably a fluorescent labeled derivative, under suitable condition for said derivative to penetrate in said cells, whereby said labeled paclitaxel derivative binds to microtubules of cancer cells, thereby preventing cell division;
b) washing off said cells from unbound labeled paclitaxel derivative; and
c) detecting a label on said labeled paclitaxel derivative bound to cancer cell, whereby detection of said label is indicative of apoptotic cancer cells.

DETAILED DESCRIPTION OF THE INVENTION

To increase solubility, while preserving cytotoxicity, in accordance with one embodiment of the present invention, there is provided a new paclitaxel derivative substituted at the 2' or 7 position of the paclitaxel molecule.

In accordance with a preferred embodiment of the invention, there is provided a water-soluble paclitaxel derivative having the following formula:

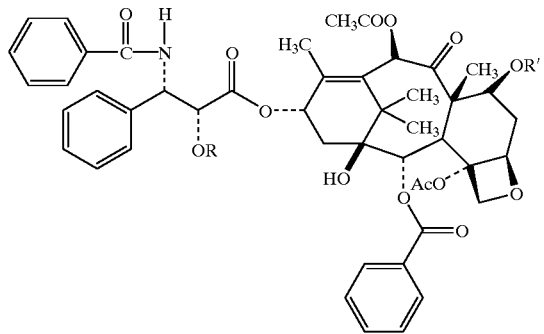

wherein R and R' are defined in the Table I below.

TABLE I
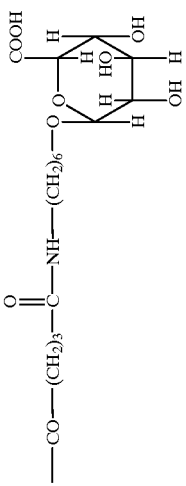

TABLE I-continued
| Compound | R | R' |
|---|---|---|
| 13) 2'-FITC-paclitaxel | 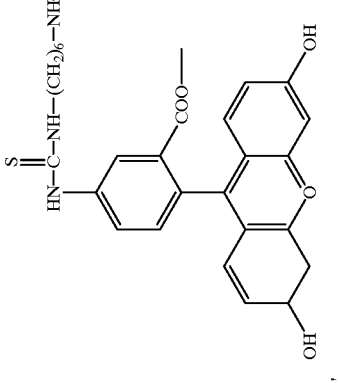 | H |
| 14) 7-FITC-paclitaxel | H | 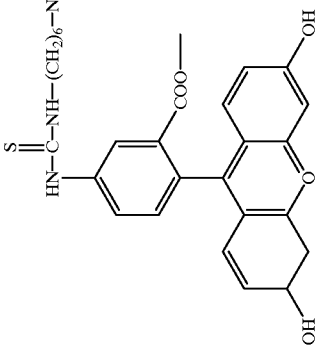 |

TABLE I-continued

| Compound | R | R' |
|---|---|---|
| 15) 2'-BODIPY-paclitaxel | NH—(CH₂)₆—NH—CO—(CH₂)₃—COO— [BODIPY structure] | H |
| 16) 7-BODIPY-paclitaxel | H | NH—(CH₂)₆—NH—CO—(CH₂)₃—COO— [BODIPY structure] |

SYNTHESIS OF DERIVATIVES

2'glutarylpaclitaxel

2'glutarylpaclitaxel was prepared according to a modification of an already reported method by Deutsch et al. Briefly, 100 mg of paclitaxel dissolved in 1.2 ml of pyridine was added to 140 mg of glutaric anhydride. After 90 minutes of reaction at room temperature the solvent was evaporated to dryness. The residue was treated twice with water and the supernatant discarded. The precipitation from acetone gave 80 mg of an impure product. Further purification was made by reverse phase HPLC on a NOVA-PAK phenyl column 0.8/10 cm from Waters RCM. The solvent system was composed of methanol, acetonitrile and water. The gradient of acetonitrile and water was linear going from 10% to 35% in 30 minutes, methanol remaining constant at 40%. The reaction was followed by TLC on a silica plate, the eluant was composed of chloroform/methanol/water (40/13/2). Detection was made with vanillin (CARDELLINA II., J. H., *J. Liq. Chromatogr.*, 14, 659–665, 1991). The reaction generates a product with an Rf of 0.74. The Rf of paclitaxel is 0.95 in the same conditions.

Figure 1:
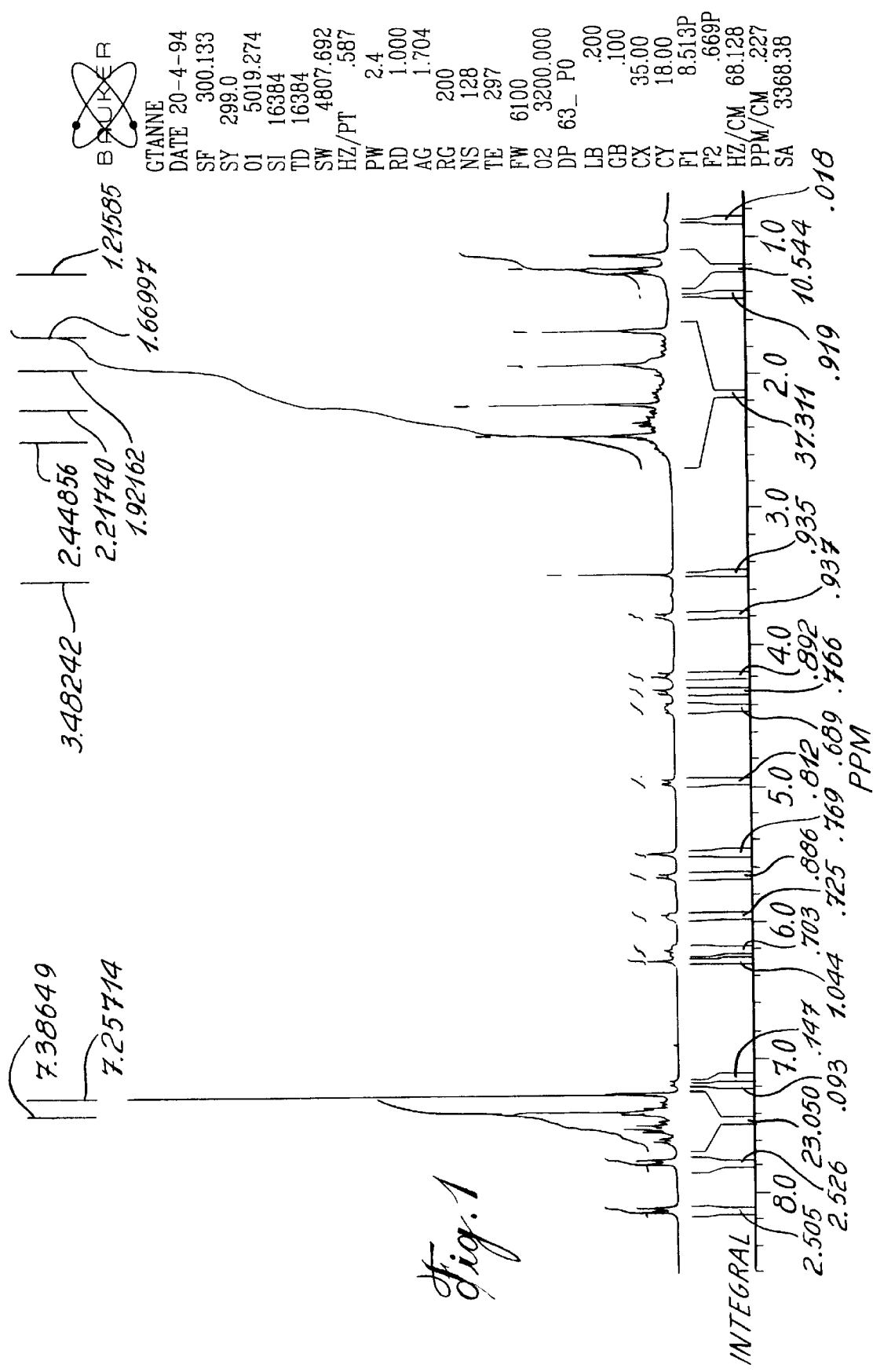
FIG. 1 illustrates the H-NMR of 2'-glutarylpaclitaxel.

The $^1$H-nmr spectrum of glutarylpaclitaxel (FIG. 1) has shown a shift of the resonance of the C-2' proton from 4.71 to 5.77 ppm (KINGSTON, D. G., et al., *J. Nat. Prod.*, 1–13, 1990; and MELLADO, W., et al., *Biochem. Biophys. Res. Commun.*, 105, 1082–1089, 1984). In the present invention, the same shift from 4.78 ppm to 5.51 ppm was observed.

2'glutaryl hexanediamine paclitaxel: "taxamine"

To 1 μmol of 2'glutarylpaclitaxel dissolved in 100 μl of acetonitrile was added 5 μmol of carbonyl diimidazole (CDI). The mixture was heated to 45° C. during 15 minutes. After cooling to ambient temperature 5 μmol of 1,6-hexanediamine was added and reaction mixture was left at room temperature for one hour. The reaction was analyzed by TLC using two different solvent systems (acetonitrile:chloroform: water or chloroform:methanol:water). Two silica plates were prepared and the samples deposited in duplicate. Vanillin detection was made on one half of each plate and ninhydrine revelation on the other half to reveal the amine component. The two systems have detected a new product with the rf of 0.12 and 0.45, respectively in the two solvent systems. The excess of 1,6-hexanediamine was eliminated by washing. Further purification was made by reverse phase HPLC in the same conditions as for 2'glutarylpaclitaxel.

2'-glutarylpaclitaxel 6-aminohexanol glucuronide

First, a glucuronide moiety must be activated. To do so 112.6 mg (0.3 mmole) of methyl 1,2,3,4 tetra-O-acetyl-β-D-glucuronate was added to HBr 30% in acetic acid. The reaction proceeded overnight in the dark at 4° C. to give methyl (2,3,4-tri-O-acetyl-1-bromo-1-deoxy-α-D-glucopyroanosid)-uronate. The solvent was dried on a "SpeedVac" vacuum (Savant Instruments Inc., Holbrook, N.Y.) and ethanol 95% was added to the residue and left two days in the dark at 4° C. The mixture was centrifuged, the supernatant discarded and 1 ml of nitromethane was added to the pellet.

The synthesis of 6-aminohexanol glucuronide is then performed. Methyl (2,3,4-tri-O-acetyl-1-bromo-1-deoxy-a-D-glucopyroanosid)-uronate was added to 81.8 mg (0.70 mmole) of 6-aminohexanol, 59.3 mg (0.43 mmoles) of white drierite and 68.3 mg (0.27 mmole) of mercuric cyanide according to the method of Turgeon et al. (Turgeon et al., *Drug Metab. Disp.*, 20:762–769, 1992). A small amount of methanol and water was added in an attempt to achieve complete dissolution of the products. The reaction mixture was stirred overnight in the dark at room temperature and the solvent was evaporated under vacuum. 6-aminohexanol glucuronide was extracted with chloroform and the most important part of the product was collected in the organic phase.

The glucuronide derivative is then deprotected. The glucuronide was treated with 2.15 mg (39.8 μmoles) of sodium methoxyde (Omega Inc., Levis, Quebec) in anhydrous methanol. The reaction proceeded at room temperature during 24 hours with agitation.

The last part consisted in joining the deprotected 6-aminohexanol glucuronide part to glutarylpaclitaxel. Synthesis of glutarylpaclitaxel (glutaryltaxol) has been described previously. The final step consisted in activating 0.6 mg (0.62 μmole) of 2' glutarylpaclitaxel with 0.95 mg (5.9 μmoles) of carbonyl diimidazole in acetonitrile. The mixture was heated for 20 minutes at 45–50° C. and left to stand at room temperature overnight. 6-aminohexanol glucuronide was added and the reaction was allowed to proceed once more overnight at room temperature.

Figure 2A:
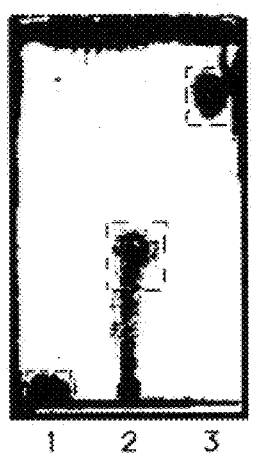
FIG. 2 illustrates the thin layer chromatography (TLC) analysis of three compounds, namely 6-aminohexanol (1), 6-aminohexanolglucuronide before deprotection (2) and methyl 1,2,3,4 tetra-O-acetyl-B-D-glucuronate (3) revealed with either molybdate (a), aniline (b) or ninhydrine(c)
Figure 2B:
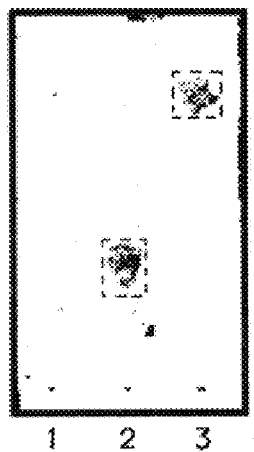
Figure 2C:
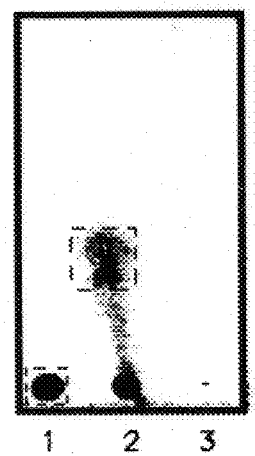

TLC was performed after the synthesis of 6-aminohexanol glucuronide. Sample and standards were applied on silica plates. Migration was performed in chloroform:acetonitrile (7:3). Chromatograms were revealed with three different solutions: ammonium molybdate+ceric sulfate in 10% sulfuric acid, solution prepared by dissolving 75 g of ammonium molybdate and 49 g. of ceric sulfate in 500 ml of 10% sulfuric acid, aniline prepared by mixing one volume of solution 1 (130 μl aniline in 5 ml acetone), with one volume of solution 2 (60 μl phosphoric acid with 2 ml acetic acid and 3 ml acetone) and 4% ninhydrine in 95% ethanol. FIG. 2 shows the thin layer chromatography (TLC) analysis of three compounds, namely 6-aminohexanol (1), 6-aminohexanolglucuronide before deprotection (2) and methyl 1,2,3,4 tetra-O-acetyl-β-D-glucuronate (3) revealed with either molybdate (a), aniline (b) and ninhydrine (c). TLC analysis showed that the glucuronide moiety was effectively attached to 6-aminohexanol (FIG. 2). A positive reaction with ninhydrin indicates that the glucuronide position is attached to the hydroxyl group of 6-aminohexanol which frees the amino group to form a peptide link with the carboxyl group of glutarylpaclitaxel.

The purification of the product glutarylpaclitaxel 6-aminohexanol glucuronide was performed on a Sephadex™ G-10 with a mixture of ethanol:water (1:1). The elution was monitored by ptical density at 227 nm.

Figure 3:
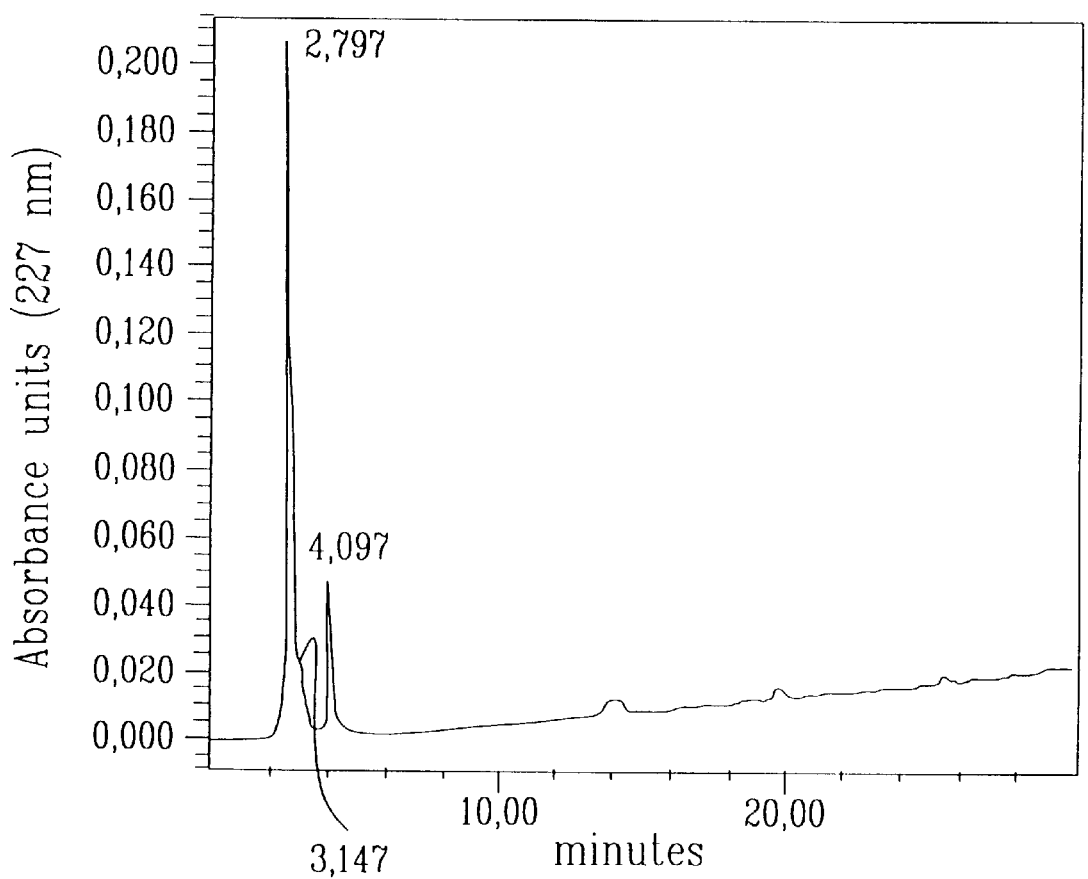
FIG. 3 illustrates the elution of the derivative 2'-glutarylpaclitaxel 6-aminohexanol glucuronide on HPLC.
Figure 4A:
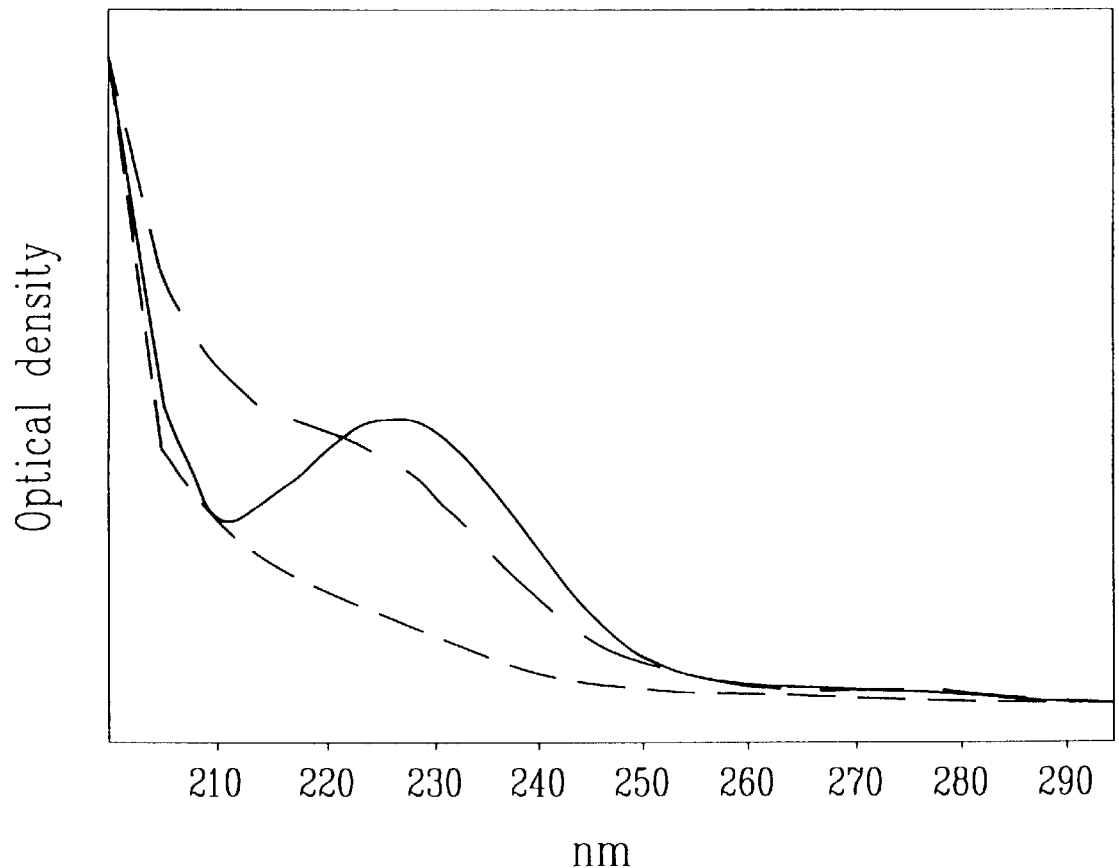
FIGS. 4A and 4B illustrate absorption spectra for the different peaks obtained during purification of glutarylpaclitaxel 6-aminohexanol glucuronide on HPLC at 2.797 minutes, 3.147 minutes and 4.097 minutes (4A) and paclitaxel (4B)
Figure 4B:
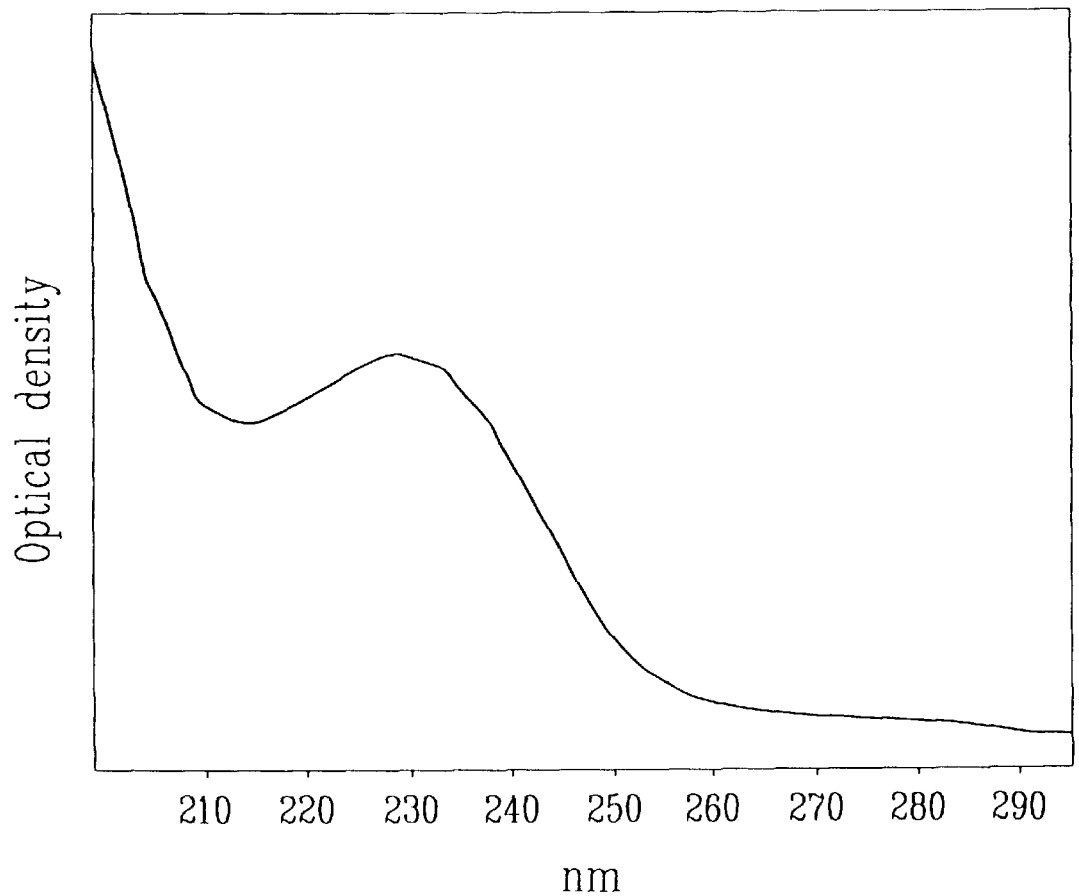

The product collected was purified by HPLC on a NOVA PAK™ phenyl reverse phase column. The system used was the Waters 625 LC System and a W996 photodiode array detector. The product was eluted with a gradient of acetonitrile:water:methanol from 10:50:40 to 45:15:40. The flow rate was 1 ml/min. during 30 minutes. The elution was monitored at 227 nm. The product was collected and evaporated to dryness on a SPEED VAC™ vacuum. FIG. 3 illustrates the elution of the derivative glutarylpaclitaxel 6-aminohexanol glucuronide on HPLC and, FIG. 4A illustrates the spectrum for the different peaks obtained during the elution of glutarylpaclitaxel 6-aminohexanol glucuronide on HPLC. HPLC analysis of the final product (FIG. 3) showed the appearance of a new compound after four minutes. This new derivative showed an absorption spectrum similar to the one of paclitaxel (FIG. 4B). Furthermore, it was less strongly retained on an HPLC hydrophobic column than paclitaxel and 2'-glutarylpaclitaxel (elution after 4 minutes versus 18 to 20 minutes). This indicates an improved aqueous solubility compared to the parent compound. Two other peaks were also present but their absorption spectra indicate that they were not taxanes.

Amino Acid Derivatives of Glutarylpaclitaxel

Six (6) amino acid derivatives, still in accordance with the present invention, were synthesized. The first step consisted in synthesizing the glutarylpaclitaxel as reported by Deutsch et al. Briefly, after 4 to 5 hours at room temperature, a solution of 65.3 μmoles of paclitaxel and 1040 μmoles of glutaric anhydride in 4 ml of pyridine was evaporated to dryness, solubilized in a minimal volume of methanol and water, and applied on a silica reverse phase C-18™ minicolumn (PREP SEPT™ C-18). Pyridine was eluted with water and glutarylpaclitaxel with methanol. The product was evaporated to dryness on a SPEED VAC™ vacuum. To a solution of glutarylpaclitaxel (2–8 nmoles) in acetonitrile, was added a 10–20 fold excess of carbonyl diimidazole (CDI). The mixture was heated to 45° C. for twenty minutes and left to stand at room temperature overnight. A large excess (50 fold) of they amino acids asparagine, aspartate, glutamate, glutamine, glycine, or serine, dissolved in water was added, slowly over a period of twenty minutes, and the reaction proceeded at room temperature overnight.

Small quantities were purified on HPLC. A Waters 625 LC system with a W996 photodiode array detector was used. The products were purified on a reverse phase Nova Pak Phenyl column (Waters, Milford, Massachusetts). Elution was performed with a gradient of acetonitrile:water:methanol from 10:50:40 to 45:15:40. The flow rate was 1 ml/min. for 30 minutes. Elution was monitored at 228 nm. For larger amounts, a silica reverse phase C-18 minicolumn ("Prep Sep" C-18 from J. T. Baker, Phillipsburgh, N.J.) was used. Products were eluted successively with water, with acetonitrile:water:methanol 10:50:40 and with the same solvents mixture, proportions being 45:15:40. Fractions of 0.5 ml were collected and analyzed on HPLC in the conditions mentioned before. The fractions containing the pure derivatives (over 90% purity) were pooled and used for in vitro assays.

Figure 6:
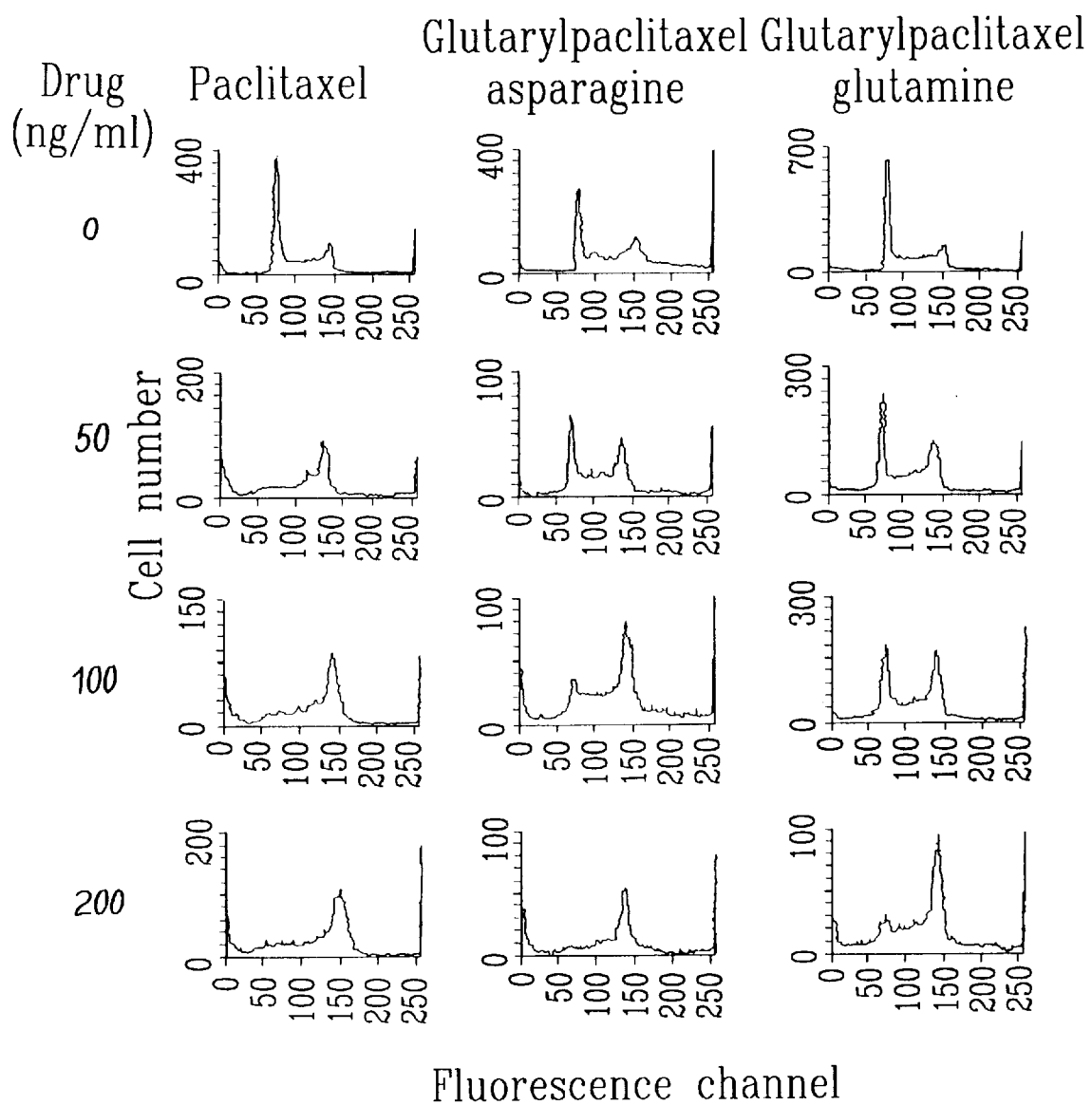
FIG. 6 illustrates the effect of the two new derivatives (glutarylpaclitaxel asparagine and glutarylpaclitaxel glutamine of the present invention on murine melanoma B-16 cell cycle.

Of all the derivatives synthetized, the preferred compounds are the asparagine and glutamine derivatives (FIG. 6). Syntheses were successful and the yields varied from 80 to 100% for the glutarylpaclitaxel synthesis and around 60% overall for the asparagine and glutamine derivatives. The products were purified as described above. The new compounds were much less retained on HPLC (elution at 3 to 6 minutes) compared to glutarylpaclitaxel and paclitaxel (20–22 minutes). The absorption spectra were similar to that of paclitaxel and mass spectra analysis of the serine derivative showed that the taxane ring was intact indicating that the reaction occurred at the side chain 2' hydroxyl.

Fluorescent Derivatives of Paclitaxel

In a further embodiment of the present invention, fluorescent paclitaxel derivatives, such as 2'-FITC paclitaxel, 7-BODIPY or 7-FITC paclitaxel, were synthesized and used to develop a new flow cytometry method for the discrimination of apoptotic from non-apoptotic cells. The 2'-FITC paclitaxel was also used for the development of an immunoassay (FPIA).

2'-FITC-labeled paclitaxel was prepared by reacting 2'-glutaryl hexadiamine paclitaxel with fluorescein isothiocyanate (FITC). FITC (2.5 mg) dissolved in methanol was added to a solution of 2'-glutaryl-hexadiamine paclitaxel (500 μg) dissolved in 0.1M carbonate buffer/methanol (50:50, v/v) pH 9.0. The mixture was allowed to react in the dark for 8 hours at 4° C. The product was purified by gel permeation chromatography on a Sephadex G10 gel column (0.7/25 cm) (Bio-Rad) using a solvent system of methanol/water (50:50).

Cytotoxicity of Derivatives

Cytotoxicity assays were performed on several cell lines to determine $ID_{50}$s. The cells used were the ovarian teratocarcinoma (CRL-1572), the ovarian carcinoma (SK-OV-3) and the corresponding drug-resistant cell line (SKVLB 600), the prostate carcinoma (LNCaP), the breast carcinoma (MCF-7), the leukemia (CCRF/CEM) and the drug-resistant line (CEM/VBL 0.3), the murine melanoma (B-16) and finally, the mouse fibroblasts (3T3). The cells were maintained in RPMI 1640 supplemented with fetal calf serum 10% at 37° C., under a 5% $CO_2$ atmosphere. For the resistant cell lines, vinblastine, concentrations of 300 ng/ml for the CEM/VBL and 600 ng/ml for the SKVLB, was added to the medium.

Cells were plated at 1000 to 2000 cells per well in 96 well plates. Drugs or derivatives were added the next day ranging from 0 to 2500 ng/ml. After three to four days in contact with the drugs, the medium was removed and replaced with 100 μl per well of new medium containing Alamar Blue 5% as reported by Pagé et al. (Pagé, B., et al., *Int. J. Oncol.*, 3, 473–476, 1993). For cells growing in suspension, only 10 μl of Alamar Blue was added to the medium. The proportion of viable cells was assessed by measuring the fluorescence produced following the reduction of Alamar Blue by mitochondrial dehydrogenases (excitation: 530 nm, emission 590 nm) after two to four hours. The assays have been made in quadruplicates. Cytotoxicity was expressed as $ID_{50}$s in nmoles per liter.

TABLE 2

Relative Ratio $ID_{50}$ of derivative/$ID_{50}$ of paclitaxel

| Drugs tested | SKO V-3 | SKV LB 600 | CCR F/CE M | CEM VBL 0.3 | CRL- 1572 | MCF-7 | LNC aP | B-16 | 3T3 |
|---|---|---|---|---|---|---|---|---|---|
| paclitaxel | 1 | 1 | 1 | 1 | 1 | 1 | 1 | 1 | 1 |
| 2'-glutarylpaclitaxel | 12.3 | <1.0 | 3.7 | >1.2 | 3.7 | 6.3 | 5.2–9.0 | 9.4–42.2 | 6.2–19.4 |
| 2'-glutaryl hexadiamine paclitaxel | n/a | n/a | n/a | >1000 | 27.0 | 15.5 | n/a | 33.8 | n/a |
| glutarylpaclitaxel asparagine | n/a | | n/a | | 7.9 | n/a | 3.3 | 18.9 | 12.8 |
| glutarylpaclitaxel glutamine | n/a | | n/a | | 6.3 | n/a | 9.2 | 18.9 | 11.5 |

TABLE 2-continued

Relative Ratio $ID_{50}$ of derivative/$ID_{50}$ of paclitaxel

| Drugs tested | Cell lines | | | | | | | | |
|---|---|---|---|---|---|---|---|---|---|
| | SKO V-3 | SKV LB 600 | CCR F/CE M | CEM VBL 0.3 | CRL-1572 | MCF-7 | LNC aP | B-16 | 3T3 |
| glutarylpaclitaxel glycine | 1.2 | | 1.4 | | 0.9 | 2.7 | 1.7 | 2.3 | 2.9 |
| glutarylpaclitaxel serine | 6.0 | | 3.3 | | 2.2 | 7.5 | 6.1 | 5.3 | 3.7 |

The four derivatives tested (asparagine, glutamine, glycine and serine) showed good cytotoxic activity against several sensitive cell lines (Table 2). Cytotoxicity was similar to paclitaxel alone. The asparagine and glutamine derivatives seem slightly less active than the other derivatives on some cell lines. The $ID_{50}$s ratios for the derivatives/paclitaxel vary from 0.9 to 42.2 depending on the derivative and the cell line tested.

The biological activity of 2'glutaryl paclitaxel, 2' glutaryl hexadiaminepaclitaxel and paclitaxel was tested by evaluating their capacity to inhibit the growth of H69 cells. 2'glutaryl paclitaxel had an activity 1.5 times less than that of paclitaxel (relative activity of 0.67), 2' glutaryl hexadiaminepaclitaxel was 8 times more active than paclitaxel (relative activity of 8), while transferrin paclitaxel conjugate was 5.4 times less active than paclitaxel (relative activity of 0.18).

Figure 5:
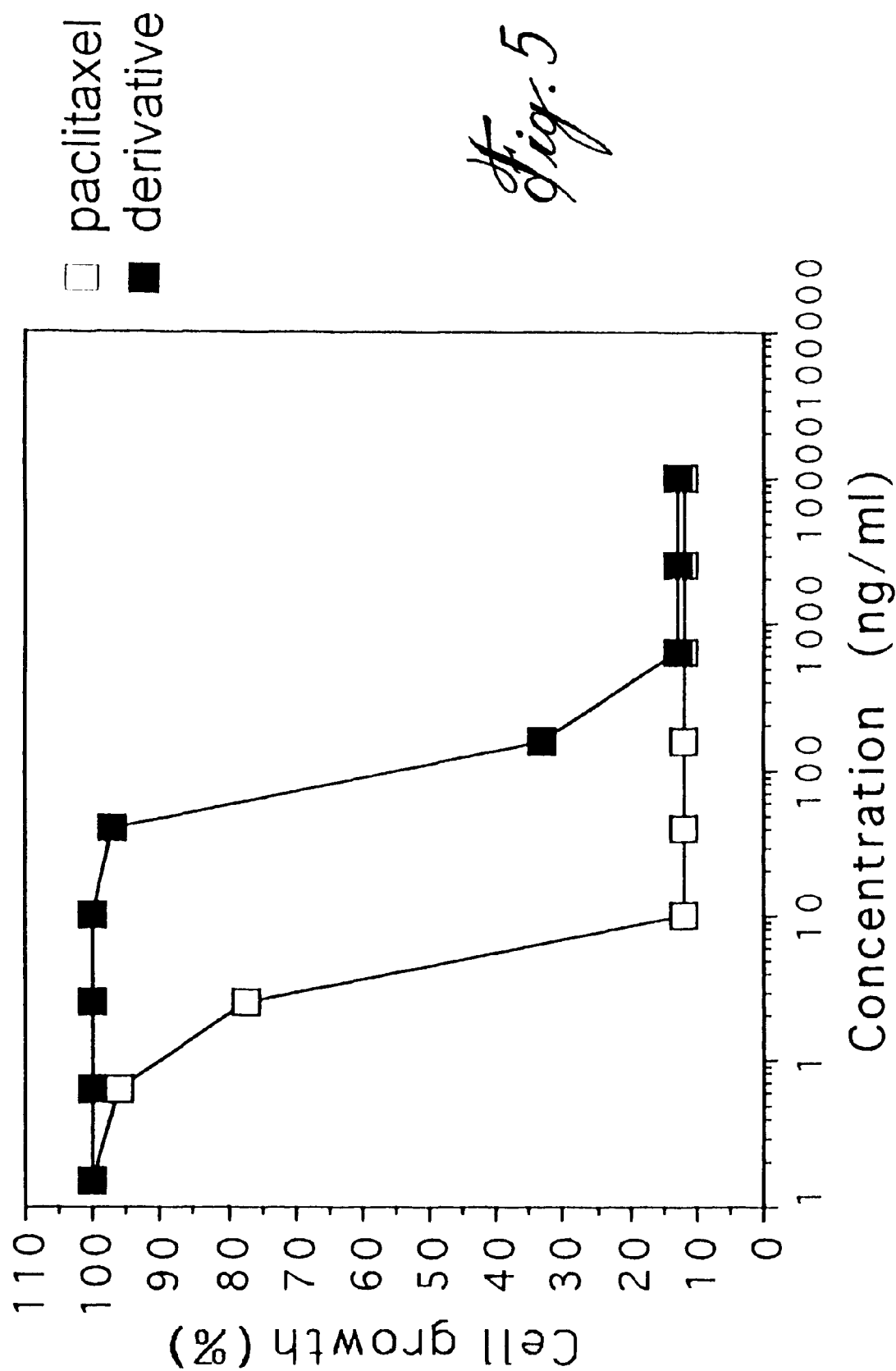
FIG. 5 illustrates the cytotoxicity of the glucuronide derivative of the present invention compared to the cytotoxicity of paclitaxel on teratocarcinoma, CRL-1572 cell line.

The $ID_{50}$s obtained were 110 ng/ml on CRL-1572 (87 nmoles/liter) for the glucuronide derivative (eluted after 4.1 minutes on HPLC) and 4.5 ng/ml (5.3 nmoles/liter) for paclitaxel, the parent compound (FIG. 5). The glucuronide derivative was about 16 times less active than paclitaxel alone.

Cell Cycle Analysis

The effect of the derivatives was assessed on the mouse melanoma B-16 cell cycle. Cells were plated, 25000 cells per well, in six well plates, incubated for 24 hours in the conditions described for the cytotoxicity assays. The next day, drugs (paclitaxel, glutarylpaclitaxel, glutarylpaclitaxel asparagine and glutarylpaclitaxel glutamine) were added, concentrations ranging from 0 to 200 ng/ml. The cells were trypsinized 24 hours later and treated with Triton X-100 0.01% for 30 minutes at 0° C. The nucleus were collected following centrifugation. The DNA was marked with 50 µl propidium iodide 1 mg/ml in 1 ml of FACS Flow (Becton Dickinson, Mississauga, Ontario). Fluorescence was measured with a cytofluorometer, FACS SORT, (Becton Dickinson, Mississauga, Ontario).

The results obtained for the cell cycle analysis show that the asparagine and glutamine derivatives block the cell cycle in prophase (G2+M) (FIG. 10) which is consistent with the results obtained for paclitaxel alone.

Solubility of Amino Acid Derivatives and Chemistry

To evaluate the solubility of the derivatives in water, the procedure as described by Swindell et al. was followed (Swindell, C. S., et al., *J. Med. Chem.*, 34, 1176–1184, 1991). Each compound was distributed between a two-phase mixture of chloroform-water and octanol-water respectively. The samples were mixed vigorously for one hour, and after separation of the two phases, each phase was examined by HPLC. (Table 3)

For the second experiment, an excess of drug was added to water. The suspension was centrifuged, the supernatant collected and analyzed for drug concentration.

The derivatives extracted with chloroform were recovered in the aqueous phase especially the asparagine derivative. For the extraction performed with octanol, the derivatives were found essentially in the organic phase. Paclitaxel alone was almost exclusively in the organic phase.

The injection on HPLC of the derivatives asparagine and glutamine revealed that the solubility of glutarylpaclitaxel asparagine and glutarylpaclitaxel glutamine was 1550 µmoles per liter and 900 µmoles per liter, respectively. The solubility obtained for the glutarylpaclitaxel and the paclitaxel were 2.6 and 0.95 µmoles per liter. The asparagine and glutamine derivatives were respectively 1980 and 947 times more soluble in aqueous solution than the parent compound.

TABLE 3

Proportion of derivatives, glutarylpaclitaxel asparagine and glutarylpaclitaxel glutamine, in organic and aqueous phases following extraction with chloroform and octanol

| | Glutarylpaclitaxel asparagine | | Glutarylpaclitaxel glutamine | |
|---|---|---|---|---|
| Chloroform extraction | 1st trial | 2nd trial | 1st trial | 2nd trial |
| Total amount extracted (nmoles) | 45.5 | 46.2 | 44.9 | 60.5 |
| Aqueous phase (nmoles) | 24 | 26 | 18 | 26 |
| Organic phase (nmoles) | 3.2 | 1.7 | 17.5 | 37 |
| Aqueous phase/organic phase | 7.5 | 15 | 1.0 | 0.7 |
| % of product recovered | 65 | 60 | 79 | 102 |
| Octanol extraction | | | | |
| Total amount extracted (nmoles) | 45.5 | 46.2 | 44.9 | 60.5 |
| Aqueous phase (nmoles) | 9.4 | 4.8 | 4.9 | 24 |
| Organic phase (nmoles) | 6.2–9.4 | 35 | 27 | 48 |
| Aqueous phase/organic phase | 1.0–1.5 | 0.7 | 0.2 | 0.5 |
| % of product recovered | 34–41 | 86 | 71 | 119 |

Hydrolysis of derivatives was performed as follows; the derivatives were incubated for two days in acetate buffer 0.1M, pH 4, at room temperature. The composition of the mixtures were analyzed by TLC. The samples were deposited on silica plates. The migration was performed in chloroform:methanol:water (40:10:5) and the chromatograms were revealed with ammonium molybdate 0.012M+ceric sulfate 0.015M in sulfuric acid 10% and with a vaniline solution prepared by mixing a solution of vaniline 1% in ethanol with phosphoric acid 3% (1:1).

It has been shown that the 2' hydroxyl is essential to tubulin binding. Intracellular hydrolysis could be responsible for the cytotoxic activity (Table 2) and effects observed on the cell cycle (FIG. 6).

Determination of Apoptotic Cells Using Fluorescent Derivatives of Paclitaxel

In accordance with one embodiment of the invention, there is provided a new method to discriminate apoptotic cells using fluorescent derivatives of paclitaxel. Cell death occurs by two main mechanims: apoptosis and necrosis. Necrosis is thought to be a non regulated mechanism occuring when a cell is subjected to harsh treatment overcoming its natural resistance while apoptosis is thought to be a controlled mechanism during which a precise sequence of reactions leads to cell death.

Apoptotic cells undergo important morphological ultrastructural and biochemical changes such as budding and bledding of the plasmic membrane, ending in the formation of apoptotic bodies. Chromatin and nuclear condensation and DNA internucleosomal cleavage are also observed.

Several methods based on the change observed in cells undergoing apoptosis have been developed to identify and quantify apoptotic cells. Morphological changes such as chromatin condensation are used in optical microscopy. In TUNEL and ISNT methods, enzymatically labeled ends of DNA fragments are used to identify apoptotic cells by flow cytometry or fluorescence microscopy.

Microtubules and associated proteins seem to play an important role in apoptosis. Martin et al. (Martin et al., *Cell Tissue Kinet.*, 23:545–559, 1990) and more recently Subrata et al. (Subrata et al., *Cancer Research*, 57:229–233, 1997) showed that the microtubule disruption induces Bcl 2 phosphorylation and apoptotic cell death while Pittman and Ireland (*Biochem. Pharm.*, 49:1491–1494, 1995) found that apoptosis is always accompanied by prominent and consistent tubulin reorganization independent of the cell cycle or the cell line, during both spontaneous and induced apoptosis. Thus, it would be highly desirable to be provided with fluorescent derivatives of paclitaxel, which bind to microtubules, to discriminate apoptotic cells.

In a further embodiment of the present invention, fluorescent paclitaxel derivatives, such as 2'-FITC paclitaxel, 7-BODIPY or 7-FITC paclitaxel, were synthesized as described above and used to develop a new flow cytometry method for the discrimination of apoptotic from non-apoptotic cells. Apoptosis was studied on peripheral human lymphocyte and CCRF CEM cells. After various periods of incubation with or without $10^{-8}$ M hydrocortisone or 1 $\mu$M of dexamethasone, cells were fixed in 70% cold methanol and double labeled either with propidium iodine and 7-FITC paclitaxel, propidium iodine and TUNEL labeling mixture (DUTP-FITC and terminal desoxynuclectidyl transferase) or TUNEL labeling and 7-BODIPY paclitaxel. Bivariate analysis of forward scatter plot versus green fluorescence (microtubules) showed that cells were distributed into two populations, one with a low forward scatter and low tubulin labeling, the second with a high forward scatter and high tubuling labeling similar to that of control cells. Propidium iodide DNA labeling and TUNEL labeling showed that the first cell population was composed of apoptotic cells while the second was normal. Double labeling with BODIPY-paclitaxel and TUNEL gave similar results. Percentage of apoptotic cells detected by the TUNEL labeling method correlated well with the percentage of apoptotic cells detected by a new assay in accordance with this particular embodiment of the present invention (correlation r=0.96). Thus, the new flow cytometric assay allows both identification and quantification of apoptotic cells.

Figure 7:
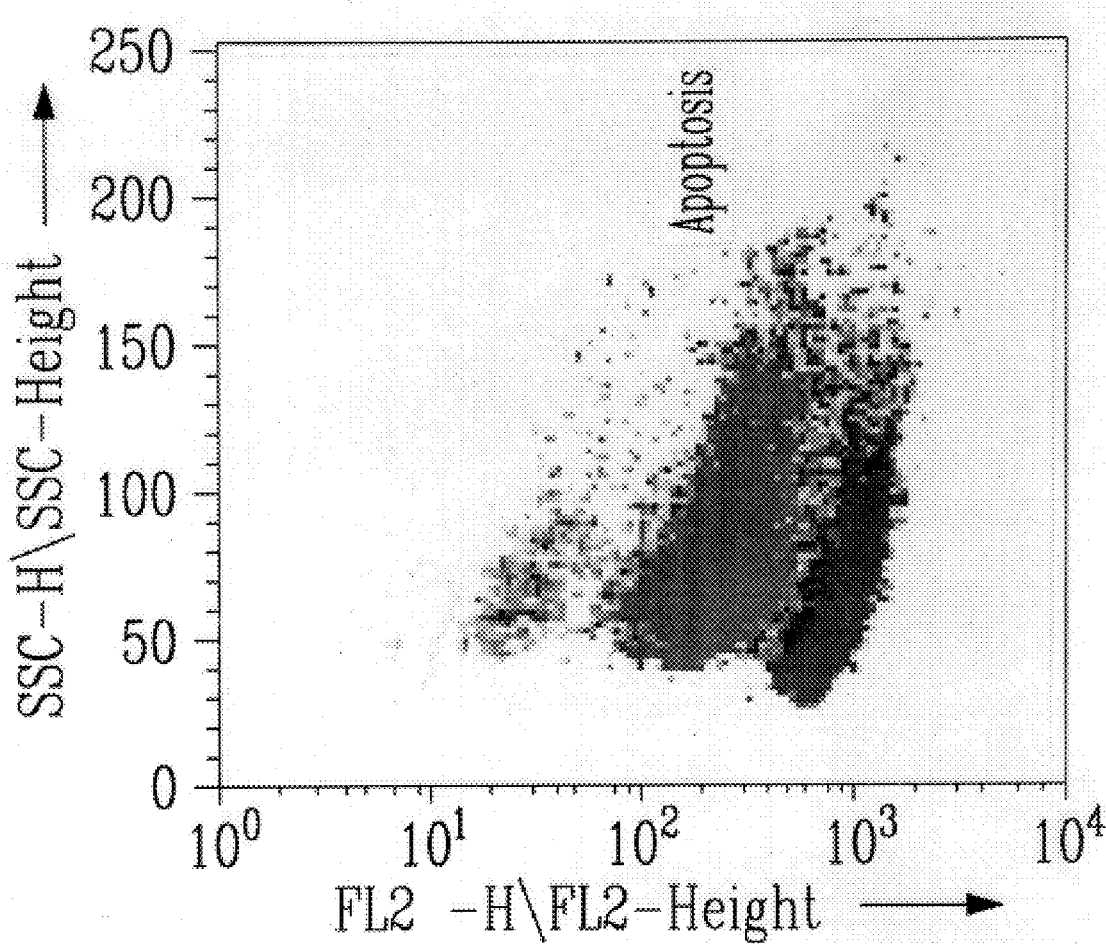
FIG. 7 illustrates apoptosis of CCRF CEM cells detected with the fluorescent 7-BODIPY paclitaxel derivative in accordance with one embodiment of the present invention.

Apoptosis of CCRF CEM cells is shown in FIG. 7. The apoptosis was induced by incubation with 1 $\mu$M dexamethasone for 72 hours. The cells were then labeled with 7 FITC-paclitaxel and analyzed by flow cytometry.

Figure 8:
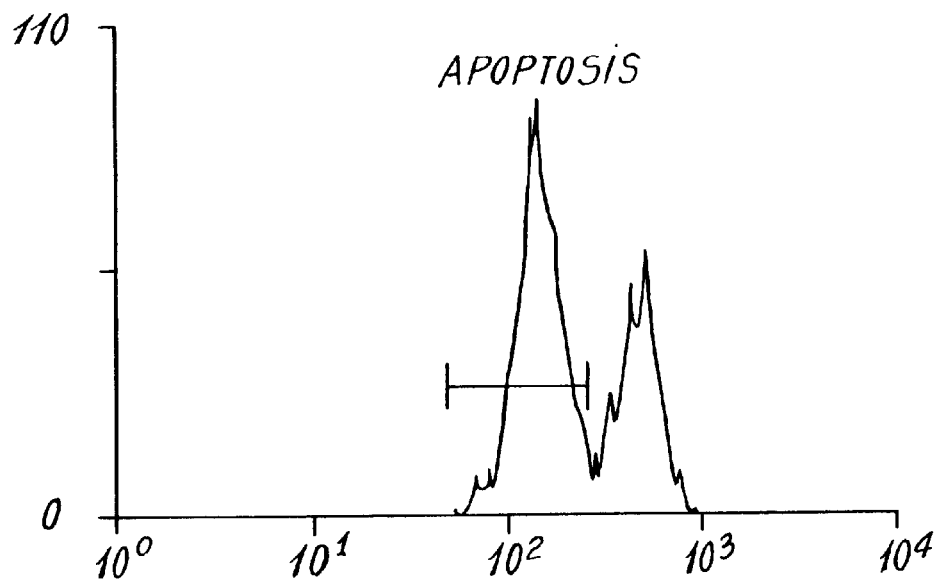
FIG. 8 illustrates the effect of a 72 hour incubation with 20 mg/ml hydrocortisone on human lymphocytes, revealed with a fluorescent 7-FITC paclitaxel derivative in accordance with one embodiment of the present invention.

The effect of a 72 hour incubation with 20 mg/ml hydrocortisone on human lymphocytes is shown in FIG. 8. The first peak of the figure around $10^2$ illustrates the apoptosis detected by labeling human lymphocytes with 7-FITC-paclitaxel.

Figure 10:
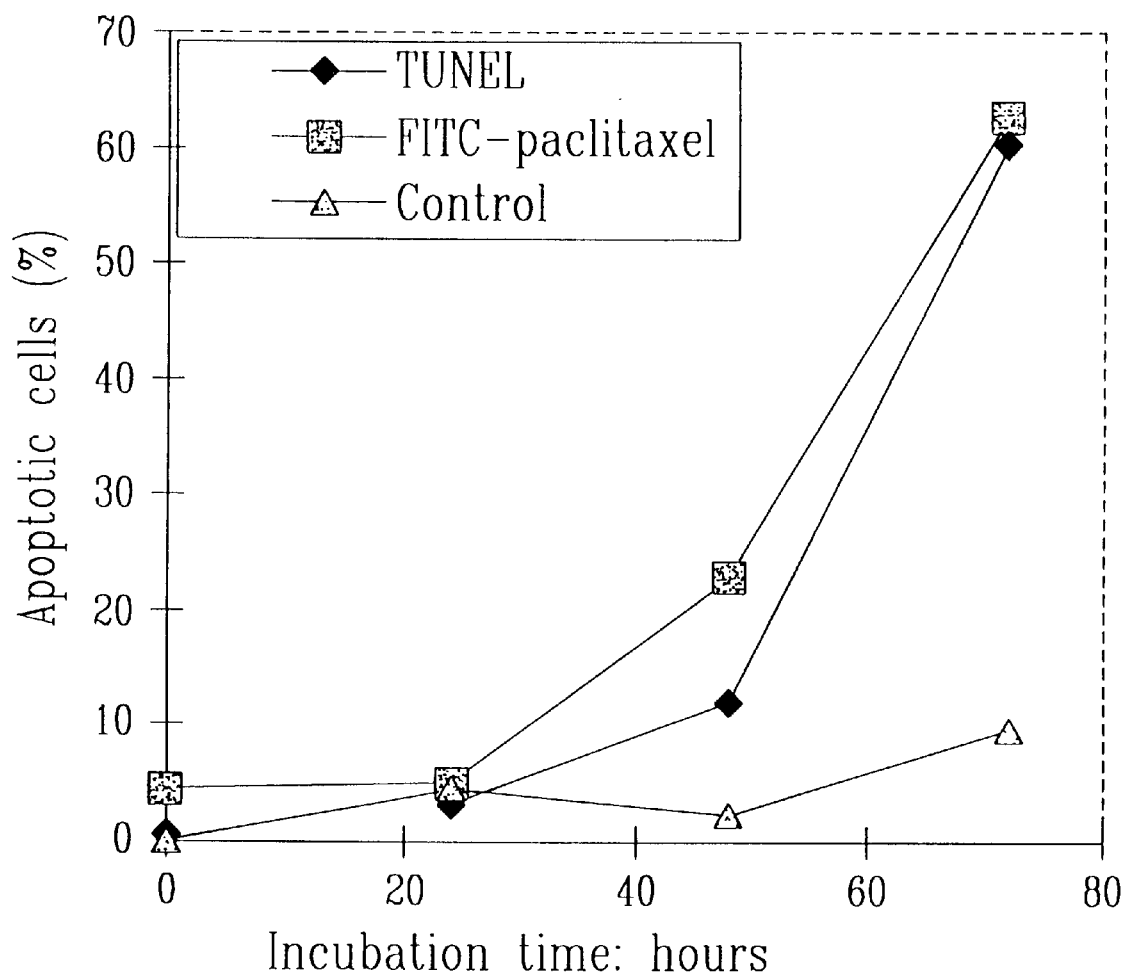
FIG. 10 illustrates the correlation of the TUNEL labeling and the 7-FITC paclitaxel derivative labeling in accordance with one embodiment of the present invention.

The correlation of the TUNEL labeling and the FITC-paclitaxel derivative labeling is shown in FIG. 10. The correlation noted between the two apoptosis methods is of 0.96. Red and green fluorescence (microtubules labeled with 7-BODIPY-paclitaxel derivative and DNA fragmentation labeled with TUNEL, respectively) was detected on double labeled CCRF CEM cells.

Figure 9:
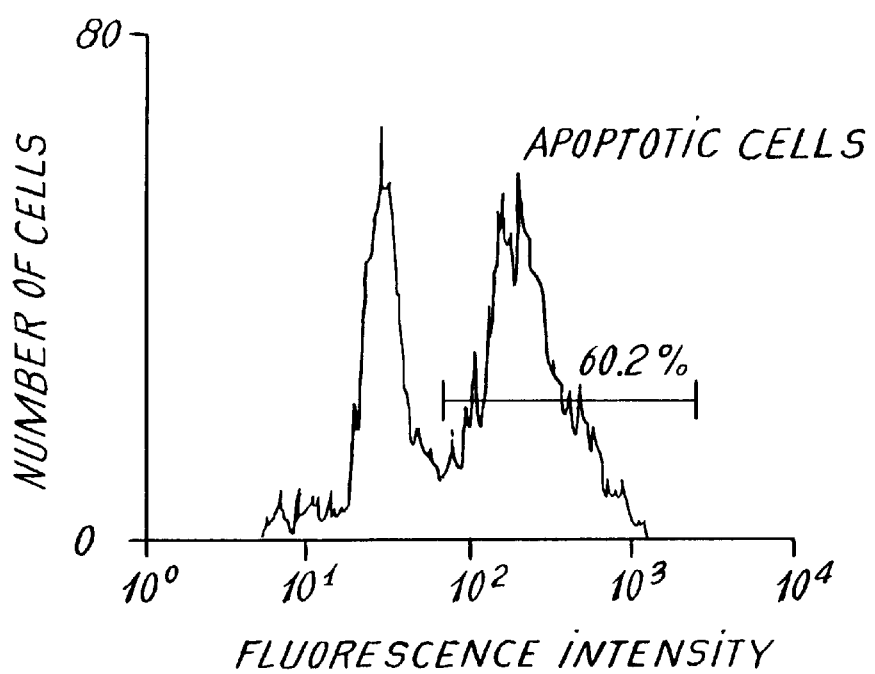
FIG. 9 illustrates the fluorescence for normal and apoptotic cells as obtained on the fluorescence activated cell sorter (FACS) using TUNEL labeling.

FIG. 9 illustrates that apoptotic cells have greater green fluorescence and less red fluorescence than normal cells.

Immunoassay for the Determination of Paclitaxel in Biological Fluids and Taxus Crude Extracts Using a Fluorescent Derivative of Paclitaxel In a further embodiment of the present invention there is provided a kit for the determination of paclitaxel in a medium. This medium may be serum, plant extracts, bacterial culture medium, etc. Accordingly, a fluorescence polarization immunoassay (FPIA) has been developed. The FPIA comprises a fluorescent derivative of paclitaxel in accordance with the present invention and an anti-paclitaxel monoclonal antibody. The fluorescent paclitaxel used in the kit of this embodiment is a 2' paclitaxel derivative coupled with FITC as described above. However, the person skilled in the art would recognize that the paclitaxel derivative coupled with any fluorescent moiety such as FITC or BODIPY in either the position 2' or 7 would be suitable to be used in the fluorescence polarization immunoassay in accordance with the present invention.

Fluorescence polarization immunoassay comprises the steps of adding the fluorescent derivative at a fixed concentration with an unknown specimen to be measured, measuring fluorescence, adding an antibody specific for paclitaxel, waiting 10 minutes and measuring polarized fluorescence on the instrument. The concentration of paclitaxel in the unknown specimen may be determined from a standard curve made from paclitaxel solutions of known concentrations.

With such a kit for the determination of paclitaxel in a medium, it was thus possible to detect paclitaxel in concentrations as low as about 2 nM. The simplicity and sensitivity of this method makes it useful for estimating paclitaxel concentration in extracts or media such as yew tree crude extracts or culture media. This sensitive method also makes the assay and/or monitoring of paclitaxel levels possible in patients under treatment.

Figure 11:
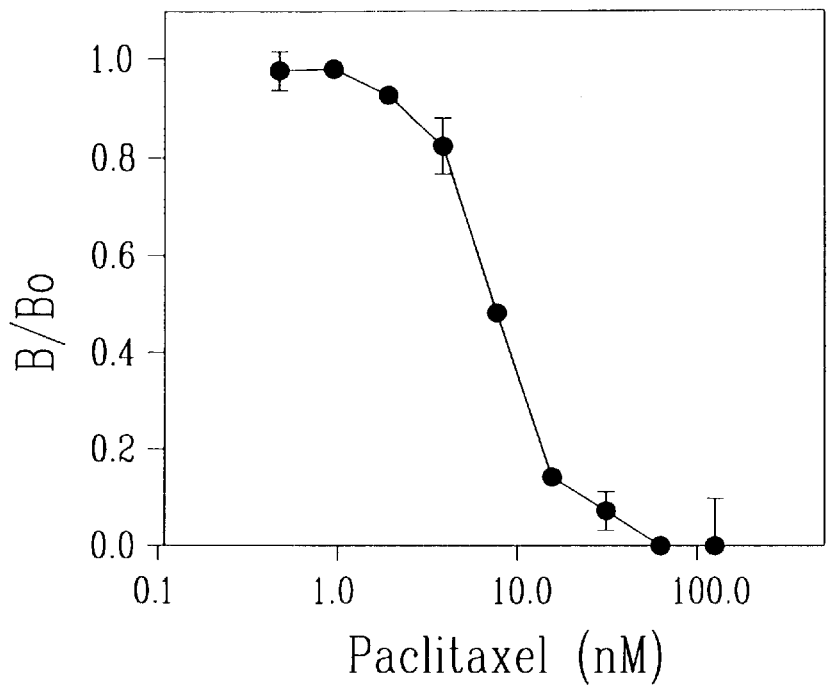
FIG. 11 illustrates a standard curve for paclitaxel concentration in bovine serum obtained with the fluorescence polarization immunoassay of the present invention.

A standard curve for paclitaxel concentration in bovine serum obtained with the fluorescence polarization immunoassay of the present invention is shown in FIG. 11. The serum dilution used in this assay was 1:20 in PBS buffer containing 0.2% sodium salicylate.

Figure 12:
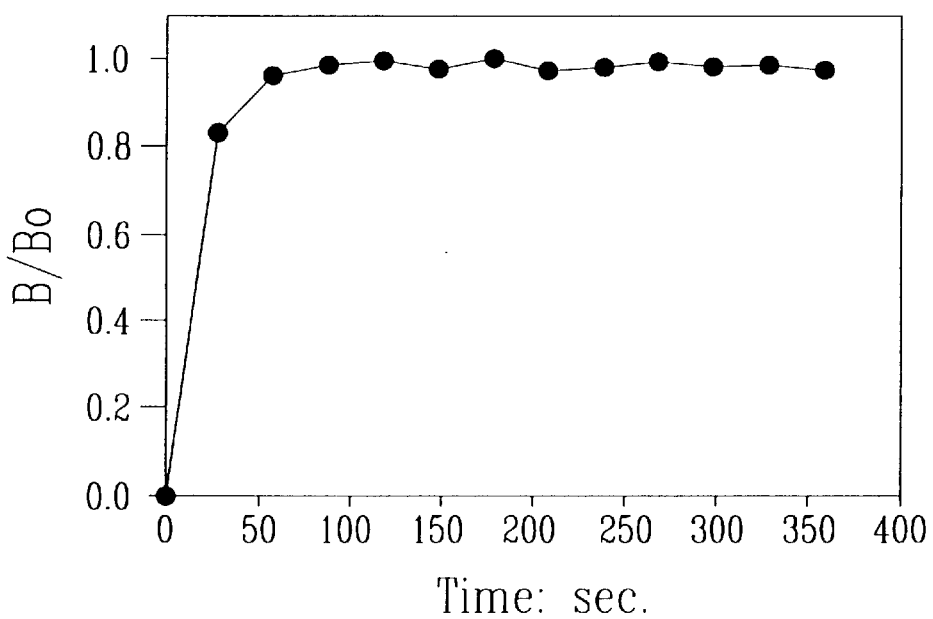
FIG. 12 illustrates the dynamic binding of 2'-FITC paclitaxel in an immunoassay in accordance with a preferred embodiment of the present invention.
Figure 13:
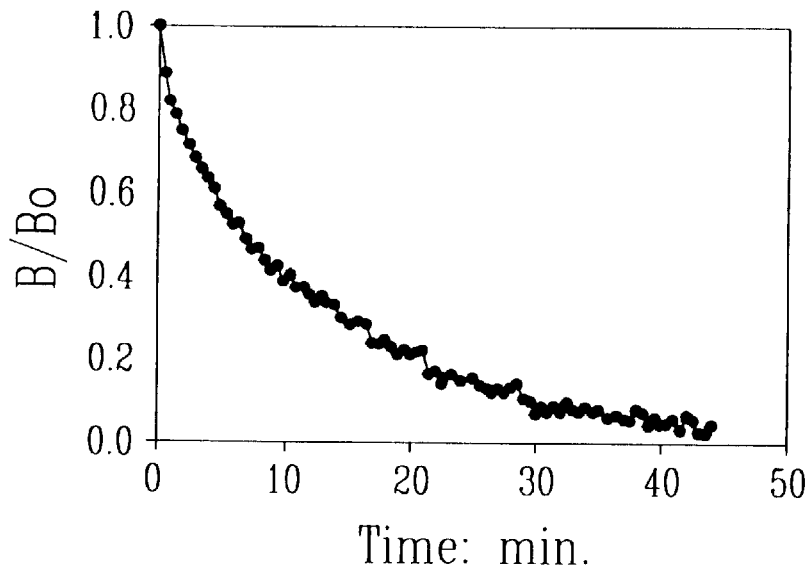
FIG. 13 illustrates the dynamic displacement of 2'-FITC paclitaxel in the immunoassay of FIG. 12.

FIGS. 12 and 13 illustrate the dynamic binding and the displacements of FITC-paclitaxel incubated with anti-paclitaxel monoclonal antibodies in PBS buffer pH 7.2 containing 0.2% sodium salicylate. After reaching an equilibrium, an excess of non-labeled paclitaxel was added. Polarization was read every 30 seconds.

The least detectable dose that could be detected with the method of the present invention was found to be about 2 nM.

Figure 14:
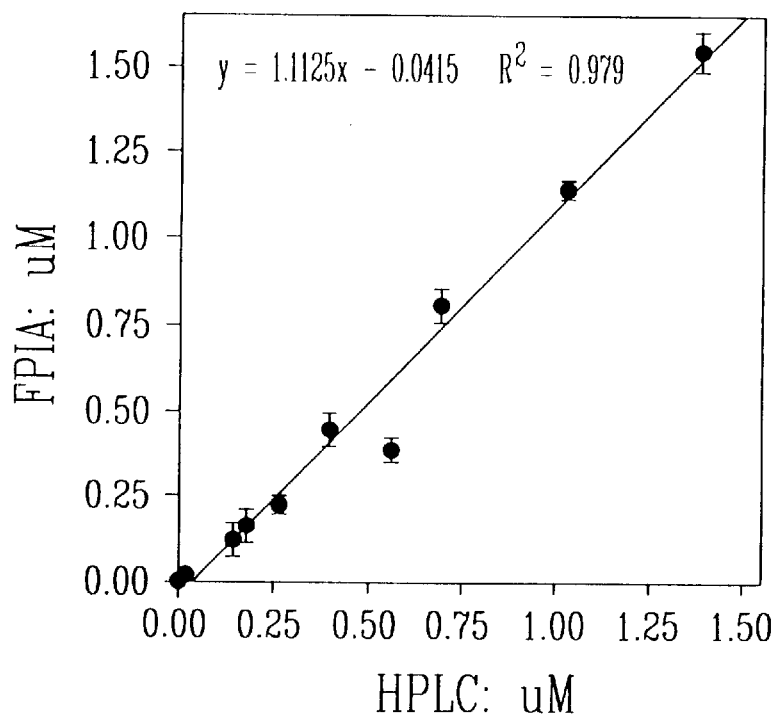
FIG. 14 illustrates the correlation of the FPIA with HPLC.

The correlation of the FPIA with HPLC is shown in FIG. 14. In this experiment to determine the correlation between FPIA and HPLC, a Erwinia taxi culture medium was spiked with known quantities of paclitaxel and extracted with 8 g of C-18 bonded silica gel. After two washes with water, paclitaxel was eluted with methanol and assayed simultaneously by FPIA and HPLC. In accordance with the present invention, the FPIA technique was successfully used to quantify paclitaxel in various media such as plant crude extracts, bacterial culture medium and bovine serum. The FPIA has a sensitivity detection limit of about 2 nM with a recovery of >96%. No matrix interference was noted at working dilutions. The FPIA technique of the present invention is a simple one step method. The FPIA could also be automated to handle a great number of samples simultaneously.

The present invention will be more readily understood by referring to the following examples which are given to illustrate the invention rather than to limit its scope.

EXAMPLE I

Synthesis of 2'glutarylpaclitaxel 100 mg of paclitaxel dissolved in 1.2 ml of pyridine was added to 140 mg of glutaric anhydride. After 90 minutes of reaction at room temperature the solvent was evaporated to dryness. The residue was treated twice with water and the supernatant discarded. The precipitation from acetone gave 80 mg of an impure product. Further purification was made by reverse phase HPLC on a NOVA-PAK phenyl column 0.8/10 cm from Waters RCM. The solvent system was composed of methanol, acetonitrile and water. The gradient of acetonitrile and water was linear going from 10% to 35% in 30 minutes, methanol remaining constant at 40%. The reaction was followed by TLC on a silica plate, the eluant was composed of chloroform/methanol/water (40/13/2). Detection was made with vanillin (CARDELLINA II., J. H., *J. Liq. Chromatogr.*, 14, 659–665, 1991).

EXAMPLE II

Synthesis of 2'glutarylhexadiamine paclitaxel

To 1 μmol of 2'glutarylpaclitaxel dissolved in 100 μl of acetonitrile was added 5 μmol of carbonyl diimidazole (CDI). The mixture was heated to 45° C. during 15 minutes. After cooling to ambient temperature 5 μmol of 1,6-hexanediamine was added and reaction mixture was left at room temperature for one hour. The reaction was analyzed by TLC using two different solvent systems. Two silica plates were prepared and the samples deposited in duplicate. Vanillin detection was made on one half of each plate and ninhydrine revelation on the other half to reveal the amine component. The two have detected a new product with the same rf in the two solvent systems. The excess of 1,6-hexanediamine was eliminated by washing. Further purification was made by reverse phase HPLC in the same conditions as for 2'glutarylpaclitaxel.

EXAMPLE III

Synthesis of glutarylpaclitaxel 6-aminohexanol glucuronide 112.6 mg (0.3 mmole) of methyl 1,2,3,4 tetra-O-acetyl-D-glucuronate was added to HBr 30% in acetic acid. The reaction proceeded overnight in the dark at 4° C. to give methyl (2,3,4-tri-O-acetyl-1-bromo-1-deoxy-a-β-D-glucopyroanosid)-uronate (Bollenbach, G. N., et al., *J. Am. Chem. Soc.* 77, 3310–3315, 1954). The solvent was dried on a "SpeedVac" vacuum (Savant Instruments Inc., Holbrook, N.Y.) and ethanol 95% was added to the residue and left two days in the dark at 4° C. The mixture was centrifuged, the supernatant discarded and 1 ml of nitromethane was added to the pellet.

Methyl (2,3,4-tri-O-acetyl-1-bromo-1-deoxy-α-D-glucopyroanosid)-uronate was added to 81.8 mg (0.70 mmole) of 6-aminohexanol, 59.3 mg (0.43 mmoles) of white drierite and 68.3 mg (0.27 mmole) of mercuric cyanide according to the method of Turgeon et al. (Turgeon, J., et al., *Drug Metab. Disp.*, 20 (5), 762–769, 1992). A small amount of methanol and water was added in an attempt to achieve complete dissolution of the products. The reaction mixture was stirred overnight in the dark at room temperature and the solvent was evaporated under vacuum. 6-aminohexanol glucuronide was extracted with chloroform and the most important part of the product was collected in the organic phase.

The glucuronide was treated with 2.15 mg (39.8 μmoles) of sodium methoxyde in anhydrous methanol (Turgeon, J., et al., *Drug Metab. Disp.*, 20 (5), 762–769, 1992). The reaction proceeded at room temperature during 24 hours with agitation.

The last part consisted in joining the deprotected 6-aminohexanol glucuronide part to glutarylpaclitaxel. Synthesis of glutarylpaclitaxel (glutaryltaxol) has been described previously. Briefly, paclitaxel was dissolved in pyridine and reacted with an excess of glutaric anhydride at room temperature for four to five hours. Pyridine was discarded when the mixture was applied on a silica reverse phase C-18 PREP SEP™ minicolumn (J. T. Baker, Phillipsburgh, N.J.) and the product was eluted with methanol. The final step consisted in activating 0.6 mg (0.62 μmole) of 2' glutarylpaclitaxel with 0.95 mg (5.9 μmoles) of carbonyl diimidazole in acetonitrile. The mixture was heated for 20 minutes at 45–50C. and left to stand at room temperature overnight. 6-aminohexanol glucuronide was added and the reaction was allowed to proceed once more overnight at room temperature.

The mixture was first eluted on a SEPHADEX™ G-10 (Pharmacia BioProcess Technology AB, Uppsala, Sweden) with a mixture of methanol:water (1:1). The elution was monitored by optical density at 227 nm.

The product collected was purified by HPLC on a NOVA PAK™ phenyl reverse phase column. The system used was the Waters 625 LC System and a W996 photodiode array detector. The product was eluted with a gradient of acetonitrile:water:methanol from 10:50:40 to 45:15:40. The flow rate was 1 ml/min. during 30 minutes. The elution was monitored at 227 nm. The product was collected and evaporated to dryness on a SPEED VAC™ vacuum.

EXAMPLE IV

Synthesis of amino acid derivatives of glutarylpaclitaxel

Six (6) amino acid derivatives, still in accordance with the present invention, were synthesized. The first step consisted in synthesizing the glutarylpaclitaxel as described above. Briefly, after 4 to 5 hours at room temperature, a solution of 65.3 μmoles of paclitaxel and 1040 μmoles of glutaric anhydride in 4 ml of pyridine was evaporated to dryness, solubilized in a minimal volume of methanol and water, and applied on a silica reverse phase C-18™ minicolumn (PREPSEP™ C-18). Pyridine was eluted with water and glutarylpaclitaxel with methanol. The product was evaporated to dryness on a SPEEDVAC™ vacuum. To the solution of glutarylpaclitaxel (2–8 nmoles) in acetonitrile, was added a 10–20 fold excess of carbonyl diimidazole (CDI). The mixture was heated to 45° C. for twenty minutes and left to stand at room temperature overnight. A large excess (50 fold) of the amino acids asparagine, aspartate, glutamate, glutamine, glycine, or serine, dissolved in water was added, slowly over a period of twenty minutes, and the reaction proceeded at room temperature overnight.

Small quantities were purified on HPLC. A Waters 625 LC system with a W996 photodiode array detector was used. The products were purified on a reverse phase Nova Pak Phenyl column (Waters, Milford, Massachusetts). Elution was performed with a gradient of acetonitrile:water:methanol from 10:50:40 to 45:15:40. The flow rate was 1 ml/min. for 30 minutes. Elution was monitored at 228 nm. For larger amounts, a silica reverse phase C-18 minicolumn ("Prep Sep" C-18 from J. T. Baker, Phillipsburgh, N.J.) was used. Products were eluted successively with water, with acetonitrile:water:methanol 10:50:40 and with the same solvents mixture, proportions being 45:15:40. Fractions of 0.5 ml were collected and analyzed on HPLC in the conditions mentioned before. The fractions containing the pure derivatives (over 90% purity) were pooled and used for in vitro assays.

EXAMPLE V

Cytotoxicity of paclitaxel derivatives

The cells used were the ovarian teratocarcinoma (CRL-1572), the ovarian carcinoma (SK-OV-3) and the corresponding drug-resistant cell line (SKVLB 600), the prostate carcinoma (LNCaP), the breast carcinoma (MCF-7), the leukemia (CCRF/CEM) and the drug-resistant line (CEM/VBL 0.3), the murine melanoma (B-16) and finally, the mouse fibroblasts (3T3). The cells were maintained in RPMI 1640 supplemented with fetal calf serum 10% at 37° C., under a 5% $CO_2$ atmosphere. For the resistant cell lines, vinblastine, concentrations of 300 ng/ml for the CEM/VBL and 600 ng/ml for the SKVLB, was added to the medium.

Cells were plated at 1000 to 2000 cells per well in 96 well plates. Drugs, concentrations ranging from 0 to 2500 ng/ml, were added the next day. After three to four days in contact with the drugs, the medium was removed and replaced with 100 μl per well of new medium containing Alamar Blue 5% as reported by Pagé et al. (Pagé, B., et al., Int. J. Oncol., 3, 473–476, 1993). For cells growing in suspension, only 10 μl of Alamar Blue was added to the medium. The proportion of viable cells was assessed by measuring the fluorescence produced following the reduction of Alamar Blue by mitochondrial dehydrogenases (excitation: 530 nm, emission 590 nm) after two to four hours. The assays have been made in quadruplicates. Cytotoxicity was expressed as $ID_{50}$s in nmoles per liter.

EXAMPLE VI

Determination of apoptotic cells using fluorescent derivatives of paclitaxel

Cells were fixed in cold 70% methanol and incubated for 10 min. on ice in 4% paraformaldehyde at room temperature for 30 minutes. Then, they were washed once with PBS and treated with 0.1% Triton X-100 for 2 minutes at room temperature, washed again with cold PBS and incubated 60 min. in the dark with appropriated dilution of the fluorescent paclitaxel (2'- or 7-FITC paclitaxel) at 37° C. Then, cells were washed with 0.1% Tween 20 in PBS. This was followed by a 30 min. incubation in the presence of 50 μg/ml of propidium iodide. Analysis was performed on a FACSort flow cytometer equipped with an argon laser set at 488 nm (Becton Dickinson). All flow cytometry data were collected and analyzed using LYSIS II software.

EXAMPLE VII

Quantification of paclitaxel from unknown samples using a Fluorescence Polarization ImmunoAssay (FPIA)

All assays were performed at room temperature. The optimal antibody working dilution was determined by incubating sequential dilutions of the antibody with a fixed amount of 2'-FITC labeled paclitaxel and the dilution giving the optimal signal was chosen as the working dilution. This dilution was then incubated with sequential dilutions of the tracer and the concentration of 2'-FITC paclitaxel giving the highest signal was chosen. 2'-FITC paclitaxel was thus used at a final concentration of 500 pg/ml and the monoclonal antibody was used at a dilution of 1:1000. For assaying, 5 μl of tracer diluted in PBS was added to 320 μl of buffer, followed by an addtional 10 μl of sample (standard or unknown). Polarization was read, each tube served as its own blank. Diluted antibody (5 μl) was added, the tubes were mixed gently, and incubated at room temperature for 60 minutes. The polarization of fluorescence was then measured.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A water-soluble paclitaxel derivative or a salt thereof having the following Formula I:

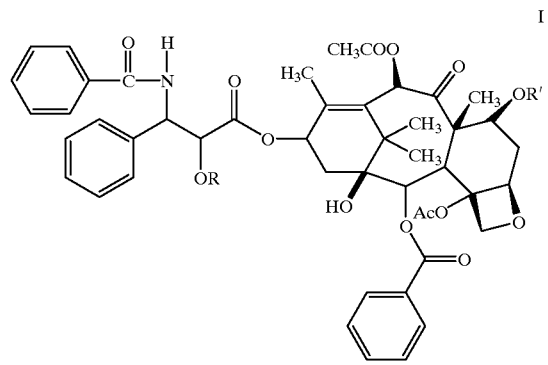

wherein R and R', identical or different, are a hydrogen or a —CO—$(CH_2)_3$—COX, in which X is selected from the group consisting of a hydroxyl, a 6-aminohexanol group, a 1,6-diaminohexyl, and a polar amino acid residue, and with the proviso that R and R' are not both hydrogen, and that R and R' are not both —CO—$(CH_2)_3$—COOH, and that R' is different than a hydrogen when R is —CO—$(CH_2)_3$—COOH.

2. The derivative of claim 1, wherein R' is a hydrogen.

3. The derivative of claim 1, wherein R is a hydrogen.

4. The derivative of claim 1, wherein the polar amino acid residue is a residue of amino acid selected from the group consisting of arginine, asparagine, aspartic acid, cystein, glutamic acid, glutamine, glycine, histidine, lysine, phenylalanine, serine, threonin and tyrosine.

5. The derivative of claim 4, wherein the amino acid residue is asparagine or glutamine residue.

6. The derivative of claim 1, wherein X is a 6-aminohexanol group.

7. The derivative of claim 1, labeled with a marker.

8. The derivative of claim 2, labeled with a marker.

9. The derivative of claim 7, wherein the marker is a fluorescent marker.

10. The derivative of claim 8, wherein the marker is a fluorescent marker.

11. A method for the in vivo treatment of cancer comprising the step of administering a therapeutically effective amount of a water-soluble paclitaxel derivative as defined in claim 1 to a patient in need of such a treatment.

12. A method for in vitro or in vivo labeling tubulin comprising the step of contacting patient's cells with a water-soluble derivative of paclitaxel as defined in claim 8.

13. A method for in vitro labeling tubulin comprising the step of contacting patient's cells with a water-soluble derivative of paclitaxel as defined in claim 7.

14. A method for in vitro determination of the concentrations of paclitaxel or paclitaxel derivative comprising the steps of;
   a) contacting a labeled paclitaxel derivative as defined in claim 7 with a biological fluid or a crude extract from a Taxus species, and an antibody raised against paclitaxel, whereby said labeled paclitaxel derivative competition for said antibody against paclitaxel in said biological fluid or said crude extract;
   b) detecting a label on said labeled paclitaxel derivative; and
   c) determining the quantity of paclitaxel from said biological fluid or said extract with respect to a standard competition curve.

15. The method of claim 14, wherein said label is a fluorescent label.

16. An in vitro method for determining apoptosis of cancer cells comprising the steps of:
   a) incubating cells with a labeled paclitaxel derivative as defined in claim 7 under suitable condition for said derivative to penetrate in said cells, whereby said labeled paclitaxel derivative binds to microtubules of cancer cells, thereby preventing cell division;
   b) washing off said cells from unbound labeled paclitaxel derivative; and
   c) detecting a label on said labeled paclitaxel derivative bound to cancer cell, whereby detection of said label is indicative of apoptotic cancer cells.

17. The method of claim 16, wherein said label is a fluorescent label.

18. A pharmaceutical composition comprising a derivative as defined in claim 1 in association with a pharmaceutically acceptable carrier.

19. A water-soluble paclitaxel derivative or a salt thereof having the following Formula I:

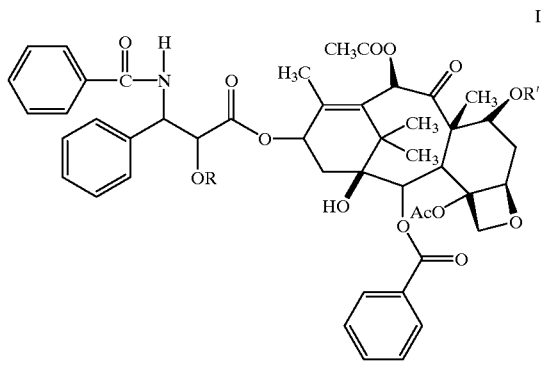

wherein R and R', identical or different, are a hydrogen or a —CO—(CH$_2$)$_3$—COX, in which X is a 6-aminohexanol group, wherein a glucoronate moiety is connected to the 6-aminohexanol group, and with the proviso that R and R' are not both hydrogen, and that R and R' are not both —CO—(CH$_2$)$_3$—COH, and that R' is different than a hydrogen when R is —CO—(CH$_2$)$_3$—COOH.

* * * * *

UNITED STATES PATENT AND TRADEMARK OFFICE
CERTIFICATE OF CORRECTION

PATENT NO. : 5,981,564
DATED : November 9, 1999
INVENTOR(S) : Michel Page; Renee Paradis; Cyrille Bicamumpaka It is certified that error appears in the above-identified patent and that said Letters Patent is hereby corrected as shown below:

On the face of the patent, please delete the Assignee "Universite Laval" and insert in its place -- BCM Development Inc.--

Signed and Sealed this

Twenty-fourth Day of April, 2001

Attest:

NICHOLAS P. GODICI

Attesting Officer

Acting Director of the United States Patent and Trademark Office